United States Patent
Gombotz et al.

(10) Patent No.: US 6,569,458 B1
(45) Date of Patent: May 27, 2003

(54) PROCESS FOR PRODUCING SMALL PARTICLES OF BIOLOGICALLY ACTIVE MOLECULES

(75) Inventors: Wayne R. Gombotz, Lexington, MA (US); Michael S. Healy, Bridgewater, MA (US); Larry R. Brown, Newton, MA (US); Henry E. Auer, Watertown, MA (US)

(73) Assignee: Alkermes Controlled Therapeutics, Inc., Cambridge, MA (US)

( * ) Notice: Subject to any disclaimer, the term of this patent is extended or adjusted under 35 U.S.C. 154(b) by 0 days.

(21) Appl. No.: 08/006,682

(22) Filed: Jan. 21, 1993

Related U.S. Application Data

(63) Continuation of application No. 07/759,604, filed on Sep. 13, 1991, now abandoned, which is a continuation of application No. 07/345,684, filed on May 1, 1989, now abandoned.

(51) Int. Cl.[7] .................................................. A61K 9/16
(52) U.S. Cl. ....................... 424/489; 424/499; 424/502; 424/600
(58) Field of Search ................................ 424/489, 499, 424/502, 600

(56) References Cited

U.S. PATENT DOCUMENTS

| 2,752,097 A | | 6/1956 | Lecher | 241/17 |
|---|---|---|---|---|
| 3,928,566 A | * | 12/1975 | Briggs et al. | 424/94.5 |
| 4,129,644 A | * | 12/1978 | Kalopissis et al. | 424/72 |
| 4,134,943 A | * | 1/1979 | Knitsch et al. | 424/468 |
| 4,357,259 A | * | 11/1982 | Senyei et al. | 424/499 |
| 4,479,911 A | * | 10/1984 | Fong | 424/497 |

FOREIGN PATENT DOCUMENTS

GB          2 077 693          6/1981

OTHER PUBLICATIONS

Himberger, D., et al., "Low–temperature Acoustic System for Inducing Nonthermal Ultrasonic Damage on Biological Targets" *Rev. Sci. Instrum.* 57(8), pp. 1681–1683 (Aug. 1986).

* cited by examiner

Primary Examiner—Gollamudi S. Kishore
(74) Attorney, Agent, or Firm—Hamilton, Brook Smith & Reynolds, P.C.

(57) ABSTRACT

Small diameter particles of biologically active molecules are produced by atomizing solutions of the molecules through a nozzle into very cold liquified gases, which immediately freeze the atomized droplets. The resulting frozen particles having diameters of approximately 10 to 90 micrometers are lyophilized to produce porous particles, suspended in a non-solvent for the molecules, and exposed to ultrasonic energy or homogenization to produce particles having diameters of 0.1 to 10 micrometers with greater than 70 to 95% of the initial biological activity of the molecules in solution.

10 Claims, 5 Drawing Sheets

PROCESS FOR PRODUCING SMALL PARTICLES OF BIOLOGICALLY ACTIVE MOLECULES

This is a continuation of application Ser. No. 07/759,604 filed on Sep. 13, 1991 now abandoned, which is a continuation of application Ser. No. 07/345,684 filed on May 1, 1989, now abandoned.

BACKGROUND OF THE INVENTION

This invention relates to processes for producing small particles of biological molecules at low temperatures using ultrasonic energy.

It is frequently desirable to incorporate biologically active proteins or other molecules within a polymeric matrix for use in controlled drug delivery or other applications requiring stable, uniform dispersions of material. Reduction of the particle size of such substances, particularly those that have biological activity such as proteins, is an important part in the design of pharmaceutical formulations.

For example, in the preparation of injectable polymeric microspheres for controlled drug delivery systems, the microspheres should be 50 micrometers or less in diameter. In order to achieve a homogeneous distribution of drug particles throughout the matrix of the microsphere, the particles should have diameters much smaller than that of the microsphere itself. Smaller diameter particles loaded in such a system will result in more desirable release kinetics and can help eliminate the initial large amount of drug that is often released (the "burst effect") from these systems. By controlling the particle size of biological molecules in a controlled release device, one can also vary the release rate of drug from these systems, as described by Brown, et al., in "Controlled Release of Insulin from Polymer Matrices", *Diabetes,* 35, 684–691 (1986).

Most small particles of compounds to be used for pharmaceutical applications are prepared using conventional techniques such as spray dying, milling, grinding and lyophilization and sieving. Each of these techniques can reduce the particle size of the materials of interest, but the diameters are often not small enough for controlled release microsphere systems. These methods also have other disadvantages. Spray drying can reduce particles to sizes of five micrometers or less, but biologically active proteins can become inactivated in the process due to denaturation at the aqueous air interface and by exposure to heat generated to evaporate the solvent. Spray drying is also inefficient and much material is lost due to sticking to the large surface area of the apparatus.

Milling and grinding can produce particles having diameters of only five micrometers, however, many of the particles are much larger in size. Because milling and grinding both require large amounts of material, these techniques are not very amenable to expensive biologically active proteins which can often be obtained only in small amounts. Milling and grinding can also result in denaturation of proteins. Sieving of lyophilized powders results in particle sizes of about 70 micrometers or greater.

It is therefore an object of the present invention to provide a method for producing small particles of biological molecules.

It is a further object of the present invention to provide particles of biologically active molecules that can be uniformly dispersed in a polymeric matrix for controlled release of the biologically active substance.

SUMMARY OF THE INVENTION

A method for producing small particles of biologically active molecules ranging in diameter from approximately 0.1 to ten micrometers which retain greater than 70% to 95% of their original biological activity, wherein the yield of particles of the biologically active molecules is 80% or greater. The technique can be used to reduce the particle size in preparations of biologically active molecules, including macromolecules such as proteins or smaller molecules such as steroids, amino acids, or synthetic drugs, while maintaining the activity of the molecules. The process can also be used to reduce the particle size of other molecules that are not biologically active, such as sugars or mixtures of these molecules with proteins.

The process for reducing the particle size of these compounds involves two principal steps. In the first step the molecules of interest are dissolved in a solvent and atomized into a low temperature liquified gas. The liquified gas is then evaporated, leaving frozen spherical particles containing solvent and the material of interest. The solvent is removed from the frozen spheres by lyophilization, resulting in the formation of porous spheres having diameters in the range of 10 to 60 micrometers. These spheres can be used as is, if larger particles are desired, or, if smaller particles are desired, they can be suspended in a non-solvent and exposed to ultrasonic energy or other mechanical forces to break the spheres into smaller particles having diameters in the range of from about 0.1 to 10 micrometers. The porous spherical particles or the smaller particles can be suspended in polymer or pharmaceutical carrier-solvent solutions and entrapped for use in drug delivery systems since the particles can be homogeneously dispersed throughout the matrix, resulting in reproducible and controllable release kinetics.

BRIEF DESCRIPTION OF THE DRAWINGS

FIG. 1 is a schematic of the formation of porous spheres of biological molecules according to the method of the present invention.

FIG. 2 is a schematic of the formation of small particles of biological molecules from the porous spheres of FIG. 1 according to the method of the present invention.

FIG. 3 is a graph of horse radish peroxidase particle size (micrometers) versus ultrasonication time (seconds), using the process of the present invention.

FIG. 4 is a graph of the mean size (micrometers) for particles of dextran versus the concentration of dextran in solution (%, w/v), when the particles are made using the processes of the present invention.

FIG. 5 shows the spectra of the second derivative of absorption with respect to wavelength of fresh hemoglobin, hemoglobin treated with the particle size reduction process of the present invention and hemoglobin denatured in 6 M guanidinium chloride.

DETAILED DESCRIPTION OF THE INVENTION

Many of the prior art methods for forming small particles of biological molecules either yield large diameter particles, result in loss of some of the material, or a cause a significant loss of biological activity. In contrast, the process of the present invention results in the size reduction of particles of biological molecules while maintaining greater than 70% of their original biological activity, and usually greater than 90–95% of the starting biological activity, as well as retaining 80% or more of the starting material.

Substances which can be used in this process include proteins, carbohydrates such as natural or synthetic polysaccharides and sugars, nucleotides, and other biologically active inorganic and organic molecules having a wide range of molecular weights. Representative examples of biologically useful polypeptides include, among others, nucleoproteins, glycoproteins, and lipoproteins. Many protein classes are suitable for use in this process, including antibodies, enzymes, hormonally active polypeptides, immune modulators such as lymphokines, monokines, and cytokines, growth regulatory proteins, blood proteins, and antigens for viral, bacterial, and parasitic vaccines. Examples of other biological molecules that can be used in this process include steroids, lipids, synthetic and naturally occurring drugs, and amino acids.

Figure 1:
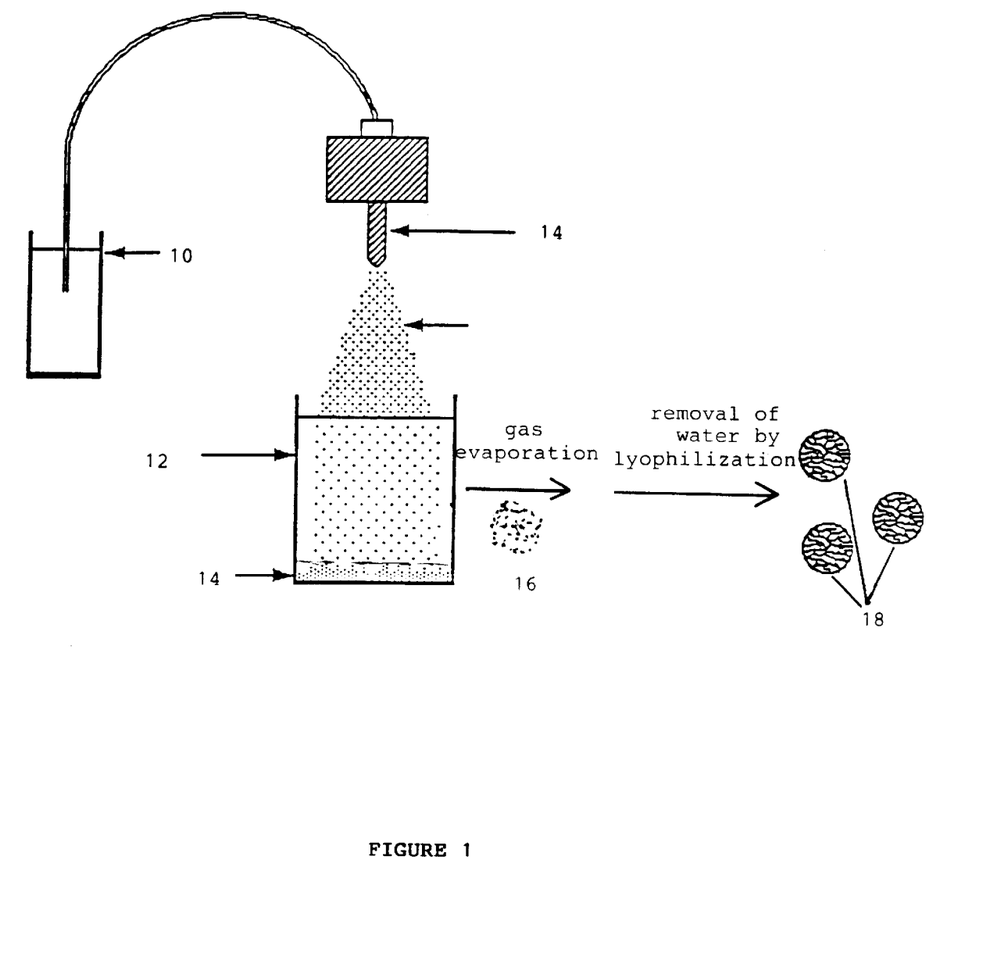
Figure 2:
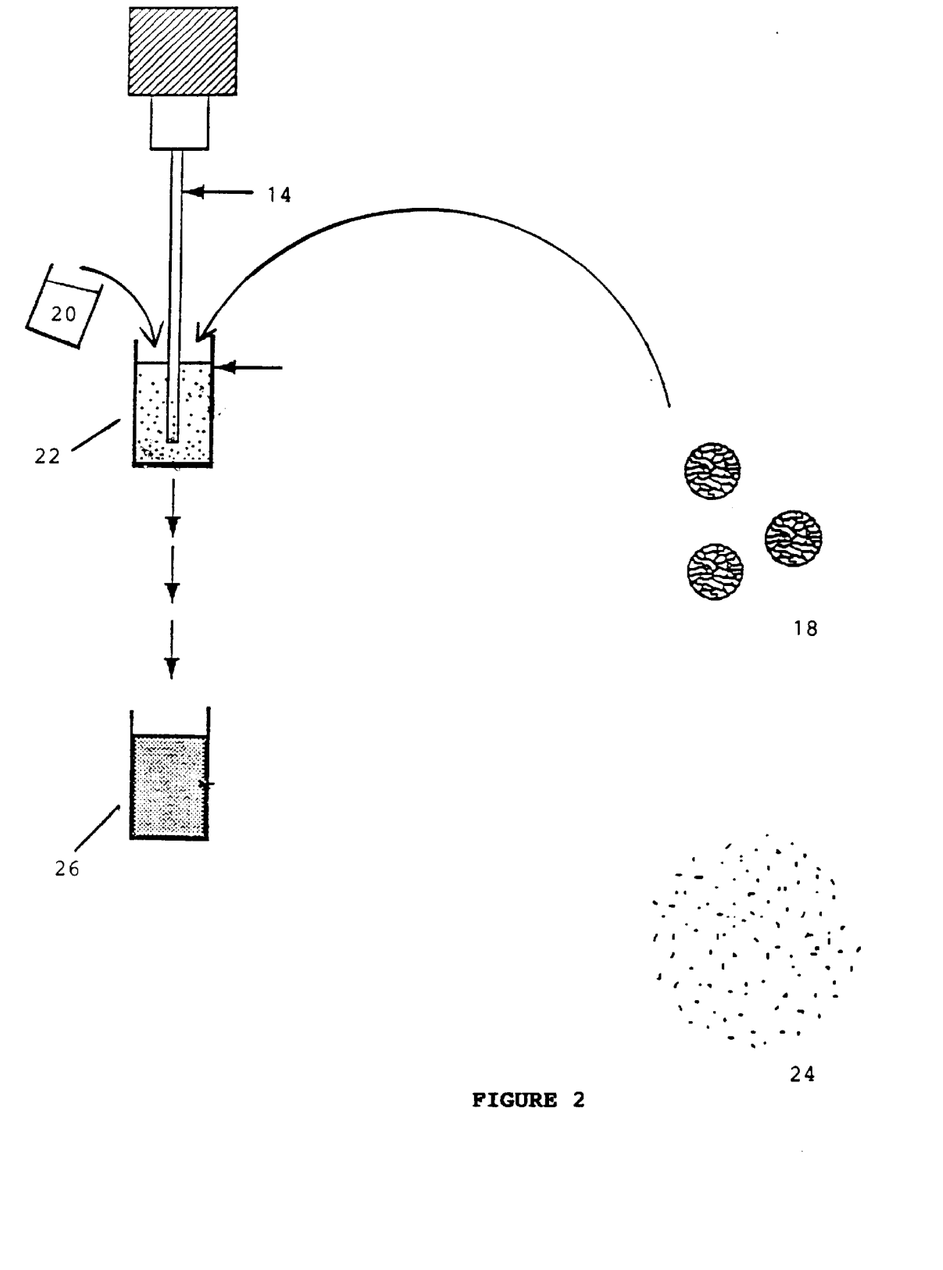
Figure 3:
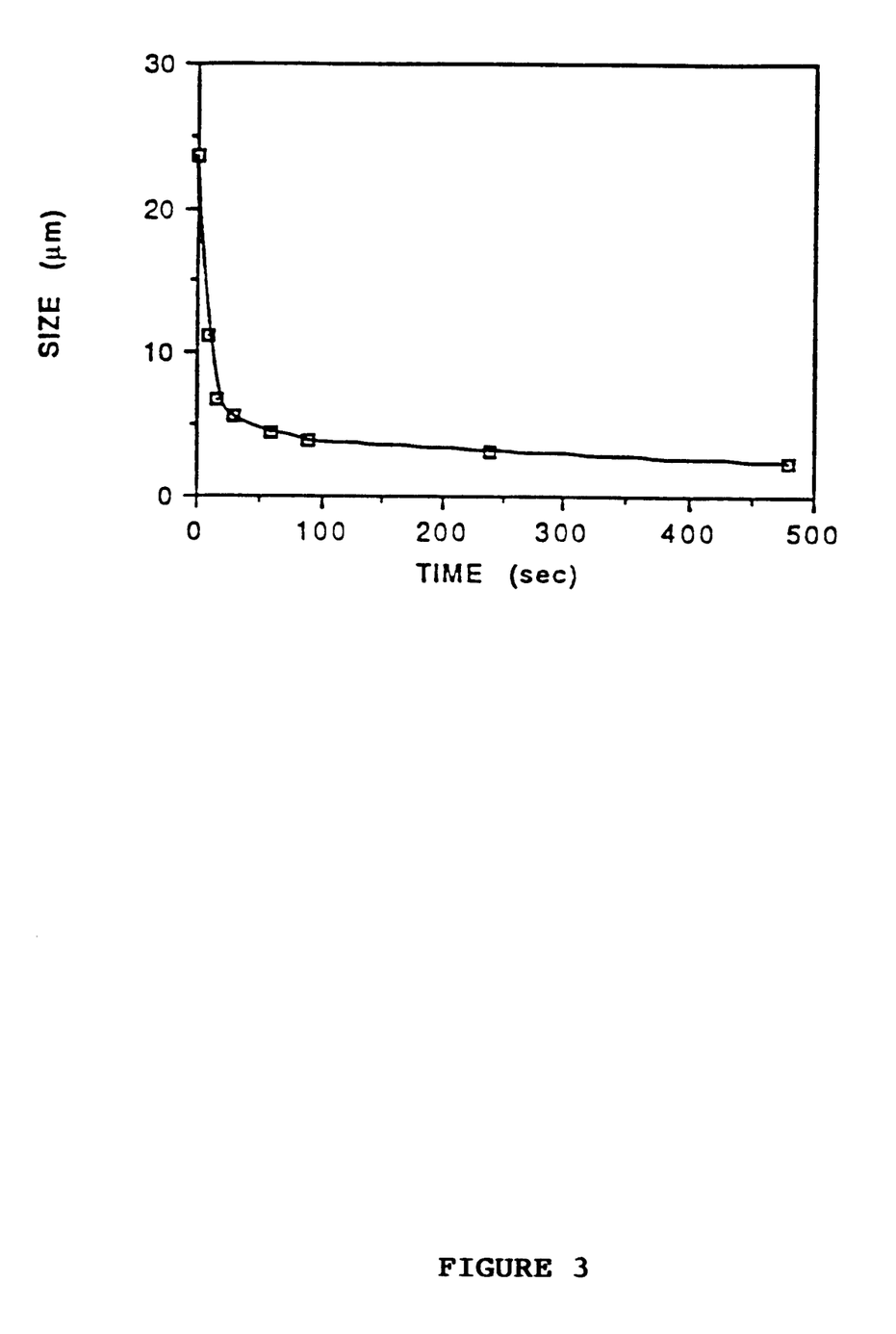

The process is shown schematically in FIGS. 1 and 2.

As depicted in FIG. 1, the biologically active molecule is first dissolved in a solvent to form a solution 10 having a concentration ranging from approximately 0.1 to 25% (w/v). The solvent must be capable of being lyophilized. The solvent may be pure water or can be buffered to a particular pH or ionic strength. The solvent may also be organic. The solution may contain a single type of molecule, mixtures of two or more types of molecules, mixtures of biologically active molecules and stabilizers, or any combination thereof. In order to reduce the particle size of certain molecules to the greatest extent, the molecule should be suspended in a medium in which not only the solvent but also the buffer salts are volatile under conditions of lyophilization. Examples of volatile buffers removed by lyophilization include ammonium bicarbonate and other ammonium salts.

The solution 10 is then atomized and the resulting droplets sprayed into a low temperature liquified gas 12 using any one of several devices 14, such as ultrasonic nozzles, pressure nozzles, pneumatic nozzles and rotary nozzles. The liquified gas 12 can be liquid argon (−185.6° C.), liquid nitrogen (−195.8° C.), liquid oxygen (−182.9° C.) or any other liquid gas that results in the immediate freezing of the atomized particles into frozen particles 14.

The droplets freeze instantly upon entering the cold liquified gas. The liquified gas 12 is removed by evaporation at a temperature at which the solvent remains frozen, leaving behind frozen droplets of solvent and biologically active molecules 16. The frozen solvent is removed from the droplets 16 by lyophilization to yield porous spheres 18. These spheres can vary in diameter depending on the technique used for their atomization, but generally range from approximately 10 to 90 micrometers.

This technique is particularly useful with proteins. When volatile buffer salts are used, the only solid remaining after lyophilization of the frozen spheres of solution containing the protein is the protein itself, with voids remaining in the space originally occupied by the volatile buffer. These voids minimize cohesion of protein-containing particles, permitting fragmentation of the protein particles into small pieces.

The porous spheres 18 can be used without further treatment if somewhat larger particle diameters are desirable. The porous spheres are useful in formulating polymeric drug delivery devices. When suspended in a polymer/solvent system in which the spheres 18 are not soluble, the result is a stable suspension 22 of the spheres 18. The choice of non-solvents that can be used for suspending the porous spheres depends on the nature of the molecules forming the spheres, as well as the polymer/solvent system. For proteins, exemplary non-solvents are acetone, ethyl acetate, methylene chloride, chloroform and tetrahydrofuran. The non-solvent for the porous spheres must be a solvent for the polymer. Exemplary polymer/solvent solutions in which proteins are not soluble include poly(lactic acid)/methylene chloride, poly(lactic-co-glycolic acid)/ethyl acetate and ethylene-vinyl acetate copolymer/methylene chloride. Such suspensions can be formed into controlled release systems in the shape of injectable microspheres or implantable matrices. These systems can be bioerodible or non-erodible.

The porous particles can also be incorporated in elixirs for medications, aerosol sprays for delivery to the lungs or nasal epithelium, suppositories, tablets and transdermal delivery systems.

As shown in FIG. 2, the size of the porous spheres 18 is further decreased by suspending the spheres 18 in a non-solvent 20 such as ethanol, acetone, methylene chloride or ethyl acetate or any other solvent in which the molecules are not soluble. The suspension 22 is exposed to ultrasonic energy or other dispersive energy sources such as homogenization, with continuous cooling, for various times to break up the porous spheres. In general, it is not desirable to subject the particles to energy in excess of that required to produce a particular diameter particle. The longer the suspension 22 is exposed to the ultrasonic energy, the smaller the size of the particles 24. This process results in the size reduction of the spheres 18 to yield particles 24 having an approximate size range of 0.1 to 10 micrometers diameter.

By selecting a non-solvent for the molecules in the particles which is also a solvent for a particular polymer, this step can be varied to produce uniform dispersions of small particles in polymer solutions, for the subsequent entrapment or encapsulation of the particles in a polymeric matrix.

The particles 24 are then removed from the sonicated suspension 26 by conventional methods known to those skilled in the art such as filtration, centrifugation or sieving. If the particles have been reduced in size in a polymer/solvent system, they can then be formed into devices such as microspheres, or processed into tablets, elixirs, aerosol sprays, suppositories or transdermal devices, using methods known to those skilled in the art.

The present invention will be further understood from the following non-limiting examples.

EXAMPLE 1

Production of Horse Radish Peroxidase Particles having diameters of less than five micrometers as a function of ultrasonication time.

A 250 mg sample of the enzyme horse radish peroxidase (HRP) (Sigma Chemical Co, St. Louis, Mo.) was dissolved in 10 ml of a 0.05 M phosphate buffer solution having a pH of 7.2. The solution was atomized through an ultrasonic nozzle (SonoTek Corp., Model 8700-60MS) into a stirred container of liquid nitrogen. The liquid nitrogen containing the frozen atomized spheres was next placed in a −80° C. freezer until the liquid nitrogen evaporated, about one to two hours. The frozen protein spheres were then placed in a lyophilizer (Virtis Company Inc., Model 10-MR-TR) for at least 12 hours to produce porous particles. After lyophilization the diameter of the HRP spheres was determined by light microscopy to be within a range of 25–35 micrometers.

A 50 mg sample of the lyophilized microspheres was suspended in 5 ml of 100 percent ethanol solution and cooled in an ice water bath to 0° C. With continuous cooling, the HRP porous particles were then exposed to an ultrasonic probe (Virtis Company Inc., Virsonic 300) for different times. Samples were analyzed for particle size diameter on a Microtrac Model 7995 Small Particle Analyzer (Leeds and Northrup). FIG. 3 shows the mean particle size plotted as a function of time of ultrasonication. Particle size decreased to under five micrometers after 100 seconds.

The activity of the HRP was determined after the lyophilization step and after the ultrasonication step. The method used to determine the enzyme activity is based upon the rate of oxidation of p-anisidine and is described in detail in *The Worthington Enzyme Manual,* Worthington, D. D., (ed.), Worthington Biochemical Corp., Freehold, N.J., p. 254 (1988). The HRP retained 90% or more of its original activity after each step of the particle size reduction process, indicating that the particle size reduction process has minimal effect on the activity of HRP.

EXAMPLE 2

Production of Zinc Insulin Particles having diameters of less than four micrometers.

The procedure in Example 1 was repeated using zinc insulin (American International Chemical, Inc., Natick, Mass.) dissolved in a 1.05 M citrate-phosphate buffer at a pH of 5.2. The mean particle diameter after five minutes sonication was 3.2±2.5 micrometers.

EXAMPLE 3

Production of Catalase Particles having diameters of less than five micrometers.

The procedure in Example 1 was repeated using catalase (Sigma Chemical Co.). The mean particle diameter after five minutes sonication was 4.5±3.3 micrometers.

EXAMPLE 4

Production of Superoxide dismutase Particles having diameters of less than three micrometers.

The procedure in Example 1 was repeated using superoxide dismutase (America International Chemicals, Inc.). The mean particle diameter after five minutes sonication was 2.7±2.1 micrometers.

The activity of the SOD was determined after the lyophilization step and after the ultrasonication step. The method used to determine the enzyme activity is based upon the ability of SOD to inhibit the reduction of nitro-blue tetrazolium by the superoxide anion. This assay is described in detail by Winterbourne, et al., in "The Estimation of Red Cell Superoxide Dismutase Activity," *J. Lab. Clin. Med.,* 85, 337 (1975). After the lyophilization step, the SOD had 94% of its original activity. After the ultrasonication step, the SOD has 91% of its original activity. This indicates that the particle size reduction process has minimal effect on the activity of SOD.

EXAMPLE 5

Production of Heparin Particles having diameters of less than seven micrometers.

The procedure in Example 1 was repeated with all the conditions as described except that the macromolecule used was heparin (Diosinth, Inc.) dissolved in deionized water. The mean particle diameter after five minutes sonication was 6.9±4.0 micrometers.

EXAMPLE 6

Production of Hemoglobin Particles having diameters of less than two micrometers.

The procedure in Example 2 was repeated using bovine hemoglobin (Sigma Chemical Co.). The mean particle diameter after five minutes sonication was 1.8±1.3 micrometers.

Example 7

Production of Hemoglobin Particles having diameters of less than two micrometers using liquid argon.

The procedure in Example 6 was repeated with all the conditions described except that the hemoglobin solution was sprayed into liquid argon before lyophilization. The mean particle diameter after 5 minutes sonication was 3.6±2.8 micrometers.

EXAMPLE 8

Production of HRP Particles having diameters of less than five micrometers as a function of pH.

The procedure in Example 1 was repeated with all the conditions as described except that three different buffers with different pH's were used to dissolve the HRP: a citrate/phosphate buffer, pH 5.2; a phosphate buffer, pH 7.2 and a tris buffer, pH 9.1. The lyophilized particles were sonicated for 5 min and their particle size determined, as shown in Table 1.

TABLE 1

| Particle Size of Sonicated HRP as a function of Buffer pH. | |
|---|---|
| Buffer pH | Particle Size ($\mu M$) |
| 5.2 | 2.9 ± 2.1 |
| 7.2 | 3.5 ± 2.8 |
| 9.1 | 6.2 ± 3.7 |

EXAMPLE 9

Production of Dextran Particles having diameters of less than five micrometers as a function of initial dextran concentration.

The procedure in Example 1 was repeated using dextran (Sigma Chemical Co., mw 40,200) at concentrations of 20, 10, 5, 1, 2.5 and 0.5 percent. The particle size of these samples was determined after being suspended in 100 percent ethanol and ultrasonicated for five minutes.

Figure 4:
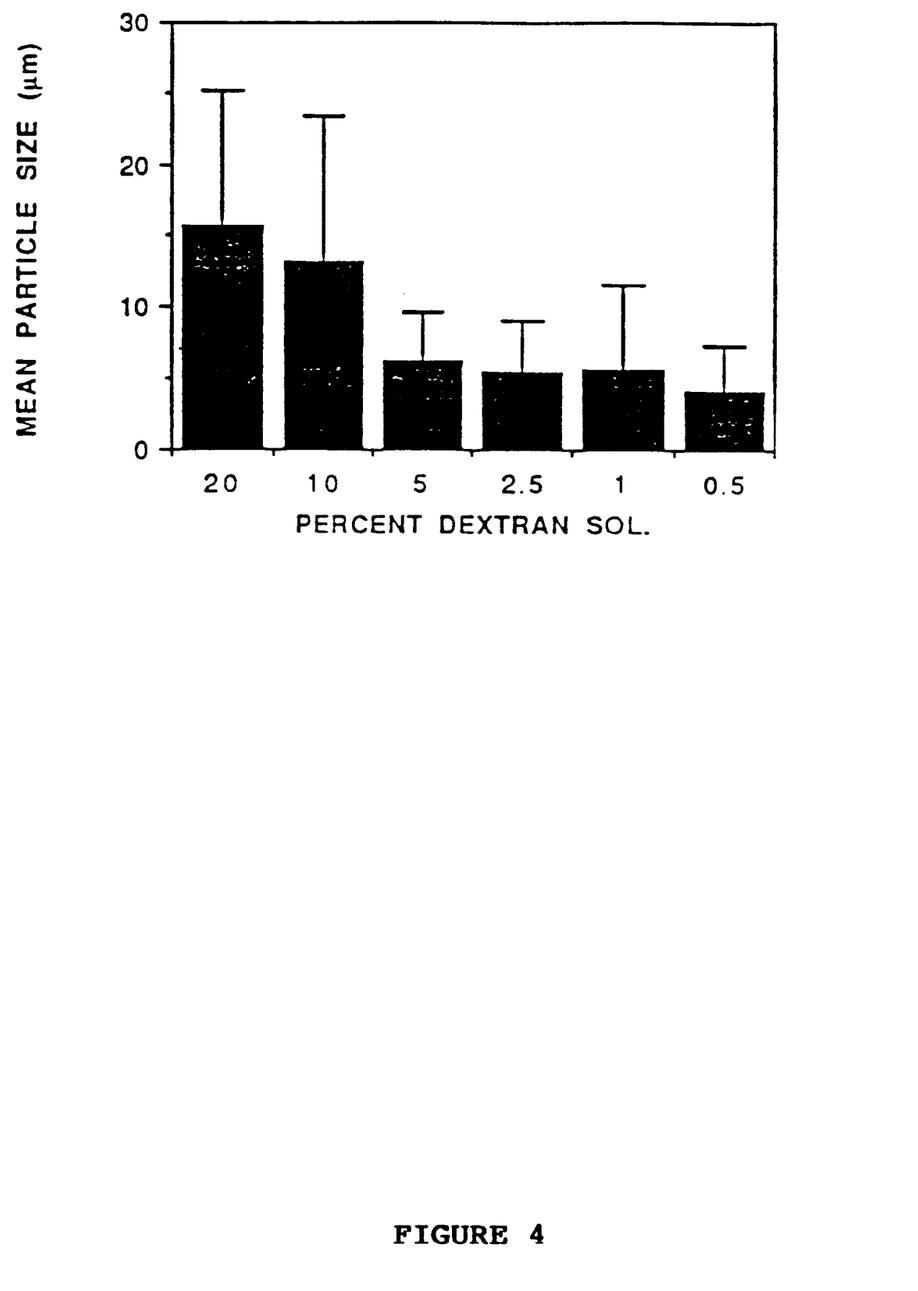

FIG. 4 shows the mean particle size of the dextran as a function of the dextran solution concentration used to make the macromolecule spheres. The results demonstrate that the smallest particles are produced using 0.5 to 5% dextran solutions.

EXAMPLE 10

Production of Superoxide dismutase-dextran Particles having diameters of less than seven micrometers.

A 125 mg sample of SOD and a 125 mg sample of dextran were dissolved in a 0.05 M citrate-phosphate buffer solution at a pH of 5.2. The aqueous solution was atomized into liquid nitrogen and processed as described in Example 1. The mean particle diameter after five minutes sonication was 6.9±6.5 micrometers.

EXAMPLE 11

Production of Hemoglobin Particles having diameters of less than four micrometers using ammonium bicarbonate as a buffer component.

125 mg bovine hemoglobin dissolved in 5 ml 0.05 M ammonium bicarbonate was formed into particles by spraying and lyophilization, according to the procedure of Example 1. Scanning electron micrographs (SEM) of the particles showed spheres having an exterior film and a spongy interior, with sizes ranging from 15 to 70 micrometers in diameter. A control solution containing only ammonium bicarbonate was also sprayed and lyophilized as described in Example 1. The absence of any solid residue after lyophilization demonstrated the volatility of the buffer salt under these conditions.

The hemoglobin particles were suspended in ethyl acetate and fragmented by subjecting them to ultrasonic irradiation with cooling by an ice bath. When the resulting particles were subjected to particle size analysis using a Leeds & Northrup Microtrac small particle analyzer, the mean particle diameter was 3.7±2.8 micrometers. SEM of sonicated particles showed flat irregular plates with lengths on the order of 1.0 micrometer, with a thickness of 0.1 micrometer.

EXAMPLE 12

Production of Hemoglobin Particles having diameters of less than seven micrometers using homogenization.

A portion of the spherical particles of hemoglobin prepared in Example 11 were fragmented by suspending them in ethyl acetate and homogenizing them using a homogenizer (Brinkmann Instruments Co., Switzerland), instead of by ultrasonic irradiation. Particle size analysis of the resulting fragmented particles gave a size distribution for the effective diameters after 80 sec of homogenization of 7.2±3.7 micrometers. After 300 sec of homogenization, the particle diameter size distribution was 6.6±3.7 micrometers.

Figure 5:
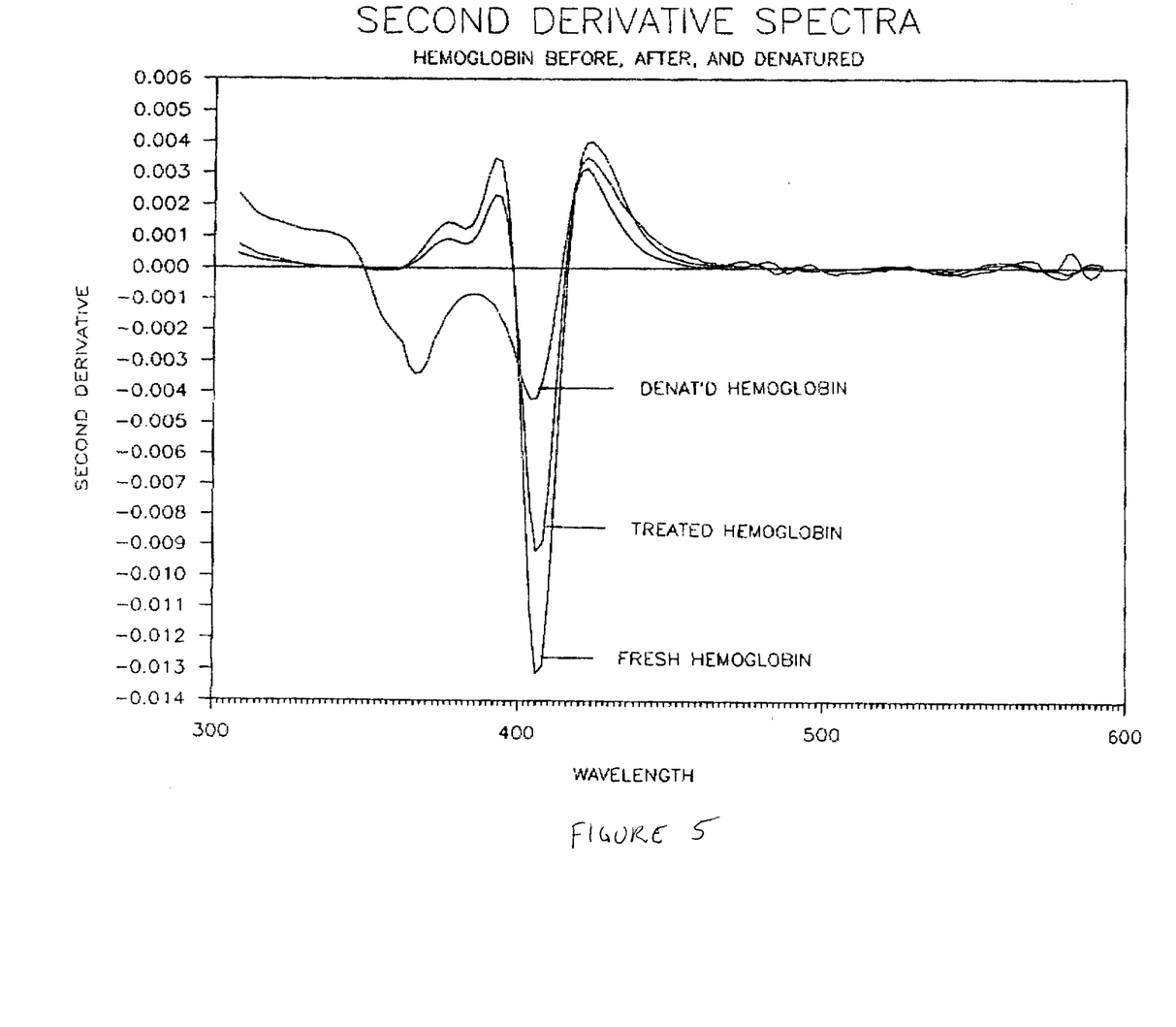

The homogenized hemoglobin particles were stored in ethyl acetate for seven days, after which the solvent was decanted and the hemoglobin dried under vacuum at room temperature. The resulting solid was dissolved in 0.2 M sodium phosphate pH 7.7, and its heme absorption compared with that of freshly dissolved bovine hemoglobin, as well as with hemoglobin denatured in 6 M guanidinium chloride, using a Hewlett Packard diode array spectrophotometer. In order to accentuate spectral features, the second derivative of absorption with respect to wavelength was obtained for each sample. The results are shown in FIG. 5. The spectra demonstrate that the samples of fresh hemoglobin and hemoglobin processed by the method described herein are identical and differ drastically from the curve for denatured hemoglobin, indicating that the particle reduction process does not cause significant alterations in the protein molecule.

EXAMPLE 13

Production of Horse Radish Peroxidase Particles having diameters of less than three micrometers using ammonium bicarbonate as a buffer component.

Horse radish peroxidase frozen particles were prepared and subjected to ultrasonic fragmentation as described for hemoglobin in Example 11. The size distribution for the effective diameters of the resulting particles was 2.8±2.2 micrometers. The HRP particles retained 90% of their activity during this process, as assayed by the method described in Example 1.

EXAMPLE 14

Production of Bovine Serum Albumin Particles having diameters of less than two micrometers using ammonium bicarbonate as a buffer component.

Bovine serum albumin (BSA) was suspended in 0, 4, 20 and 100 mg of ammonium bicarbonate/ml water to a concentration of 25 mg BSA/ml, and protein particles prepared as described for hemoglobin in Example 11. Under light microscopy, the BSA particles prepared from BSA solutions in 100 mg ammonium bicarbonate/ml solution contained extremely filamentous, airy strands of protein. The particles prepared from BSA in the other ammonium bicarbonate solutions also appeared filamentous but were more dense.

The sample prepared from 100 mg ammonium bicarbonate/ml was suspended in ethyl acetate and fragmented by ultrasonic irradiation. The resulting preparation gave a size distribution having more than 60% of the particles less than 1.7 micrometers in diameter. Under light microscopy virtually all the particles were less than 1 micrometer in size.

EXAMPLE 15

Production of Glycine Particles having a diameter of less than 3.5 micrometers.

A 2.5% solution of Glycine (EM Science) was prepared in deionized water. This was ultrasonicated to form frozen particles which were lyophilized according to the procedure of Example 1. Light microscopy revealed porous particles having a mean diameter of 24.4±14.6 micrometers. These porous particles were fragmented by ultrasonication for 4 min, producing particles having a mean diameter of 3.2±1.9 micrometers. This example demonstrates the utility of this particles for reducing the particle size of low molecular weight compounds such as glycine (75.07 daltons).

EXAMPLE 16

Production of Testosterone Particles from 1,4 Dioxane having a diameter of less than five micrometers.

The procedure in example 1 was repeated using a 2.5% solution of testosterone (Sigma Chemical Co.) in 1,4 dioxane. The resulting particles had a mean diameter of 5.4±2.9 micrometers, demonstrating the effectiveness of the procedure to prepare small particles of steroids in organic solvents.

EXAMPLE 17

Production of Stable suspension of porous BSA Particles.

A 1.994 gm sample of bovine serum albumin (BSA) (Sigma Chemical Co.) was dissolved in 80 ml of deionized water, atomized through an ultrasonic nozzle into liquid nitrogen and lyophilized. The particle diameter of the porous spheres ranged from 20–30 micrometers..

Samples of these BSA particles were suspended in a 10 percent (w/v) solution of ethylene-vinyl acetate (USI Chemicals Co.) in methylene chloride, resulting in mixtures containing 5, 10 and 20 percent by weight of protein. All of these solutions contained stable suspensions of the BSA and the BSA did not settle to the bottom of the solution with time. It is believed that the solvent diffuses into the porous particles, equalizing the density of the particles with that of the polymer-solvent solution.

Modifications and variations of the method for making biologically active, small diameter particles will be obvious to those skilled in the art from the foregoing detailed description of the invention. Such modifications and variations are intended to come within the scope of the appended claims.

We claim:

1. A process for making porous particles of biologically active molecules from particles having a diameter of approximately 10 to 90 micrometers comprising:

providing a solution of biologically active molecules selected from the group consisting of carbohydrates, nucleotides, inorganic compounds, synthetic organic molecules, polypeptides, and lipids, in a solvent that can be removed by lyophilization; atomizing the solution into a liquified gas selected from the group consisting of nitrogen, argon, and oxygen in a vessel to produce frozen particles containing biologically active molecules in combination with the solvent;

removing the gas from the vessel containing the frozen particles;

removing the solvent from the particles by lyophilization to produce porous particles having a diameter of between approximately 10 and 90 microns, suspending the porous particles in a non-solvent for the biologically active molecules, and fragmenting by exposure to dispersive energy with continuous cooling the suspension of particles until particles having diameters of approximately 0.1 to 10 micrometers and containing at least 70% of their original biological activity are produced.

2. The process of claim 1 further comprising selecting an aqueous solvent and adjusting the pH, ionic strength, and concentrations of dissolved biologically active molecules in the solution.

3. The process of claim 2 wherein volatile salts which can be removed using lyophilization are used to buffer the solution.

4. The process of claim 1 wherein the solution is atomized through an ultrasonic nozzle.

5. The process of claim 1 further comprising suspending the 10 to 90 micrometer diameter porous particles in a polymer-solvent solution selected from the group consisting of poly(lactic acid)/methylene chloride, poly(lactic-co-glycolic acid)/ethyl acetate and ethylene-vinyl acetate copolymer/methylene chloride.

6. The process of claim 1 further comprising removing the 0.1 to 10 micrometer particles from the non-solvent.

7. The process of claim 1 further comprising incorporating the 0.1 to 10 micrometer particles in a polymeric matrix.

8. Particles of biologically active molecules having a diameter of between approximately 0.1 and 10 micrometers, containing molecules having greater than 90% of the activity of the molecules in solution prior to forming the particles, wherein the particles are produced by;

providing a solution of biologically active molecules selected from the group consisting of carbohydrates, nucleotides, inorganic compounds, synthetic organic molecules, polypeptides, lipids, in a solvent that can be removed by lyophilization;

atomizing the solution into a liquified gas in a vessel to produce frozen particles having diameters between 10 and 90 micrometers containing biologically active molecules in combination with the solvent;

removing the gas from the vessel containing the frozen particles;

removing the solvent from the particles by lyophilization to produce porous particles;

suspending the porous particles in a non-solvent for the biologically active molecules; and fragmenting the porous particles into particles having diameters of approximately 0.1 to 10 micrometers.

9. The porous particles of claim 8 further comprising a polymeric matrix.

10. The porous particles of claim 9 wherein the polymeric matrix is formed of poly(lactic acid), poly(lactic-co-glycolic acid), ethylene-vinyl acetate, copolymers and blends thereof.

* * * * *